US00PP32246P2

(12) United States Plant Patent
Hansen

(10) Patent No.: US PP32,246 P2
(45) Date of Patent: Sep. 29, 2020

(54) ***AMSONIA* PLANT NAMED 'STARSTRUCK'**

(50) Latin Name: ***Amsonia* hybrid**
Varietal Denomination: Starstruck

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,014

(22) Filed: Jan. 15, 2020

(51) Int. Cl.
*A01H 5/02* (2018.01)
*A01H 6/08* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden

(57) ABSTRACT

A new and distinct *Amsonia* plant named 'Starstruck' characterized by winter-hardy, compact, densely-stemmed, clean habit with oblanceolate, medium-green foliage that goes dormant in the winter; single, periwinkle-blue, star-shaped flowers on medium-tall dark purple scapes flowering beginning about early-May and effective for about four weeks. The new plant is useful in the landscape as a specimen or en masse and also as a cut flower.

1 Drawing Sheet

Botanical classification: *Amsonia* hybrid.
Variety denomination: 'Starstruck'.

STATEMENT REGARDING PRIOR DISCLOSURES UNDER 37 CFR 1.77(B)(6)

The first non-enabling disclosure of the claimed plant, in the form of a website to the public and email release to customers, was made by Walters Gardens, Inc. on Feb. 1, 2019. Since then, Walters Gardens, Inc. used photographs and descriptions of the new plant in their "Walters Gardens 19-20 Catalog" released on May 29, 2019 and sold the first plants on Jul. 8, 2019. Walters Gardens, Inc. obtained the new plant and information about the new plant directly from the inventor. No plants of *Amsonia* 'Starstruck' have been sold, in this country or anywhere in the world, nor has any disclosure of the new plant been made more than one year prior the filing date of this application, and such sale or disclosure within one year was either derived directly or indirectly from the inventor.

BACKGROUND AND ORIGIN OF THE PLANT

The present invention relates to a new and distinct Blue Star plant, *Amsonia* 'Starstruck' hereinafter also referred to as the new plant or just the cultivar name, 'Starstruck'. *Amsonia* 'Starstruck' was hybridized by the inventor in the spring of 2011 in a trial field at a wholesale perennial nursery in Zeeland, Mich., USA. The new plant originated from a breeding program conducted by the inventor with the specific intention to improve the garden worthiness, expand color regimens and increase flowering period which were some of the criteria of further trials in the trial beds at the same nursery in Zeeland, Mich. The female or seed parent was a propriety unnamed selection of *Amsonia rigida* (not patented) and the male or pollen parent was a propriety unnamed selection of *Amsonia tabernaemontana* (not patented). Seeds from the cross were collected on Oct. 6, 2011.

The new plant was selected as a single seedling from this cross, and after confidential evaluations in a trial bed beginning in 2012 in Zeeland, Mich. the new plant resulting from a single seedling was assigned the breeder code 11-70-01 through the remaining trial period prior to assigning a cultivar name.

The new plant has been asexually propagated by shoot tip cuttings at the same wholesale nursery in Zeeland, Mich. since 2012 with all resultant asexually propagated plants having retained all the same unique traits as the original plant. *Amsonia* 'Starstruck' has proven to be stable and reproduces true to type in successive generations of asexual reproduction.

The most similar known Blue Star cultivar is 'Storm Cloud' (not patented). 'Storm Cloud' is taller in habit, with darker purple in the stems, wider foliage with more significant silver veining, with earlier and longer branching, not as compact flowering and a flowering season that begins one to two weeks earlier. The female parent is taller with a more open habit, broader foliage, and has soft blue flowers on darker stems. The male parent is slightly taller with wider foliage. The new plant can also be compared with 'Blue Ice' (not patented) which has a shorter more spreading habit compared with the new plant.

*Amsonia* 'Starstruck' differs from all other Blue Star plants known to the applicant, by the combination of the following traits:

1. Periwinkle-blue star-shaped flowers in clusters near the end of the stems;
2. Flowering above the foliage in mid-spring on dense panicles for about three to four weeks.
3. Winter-hardy to USDA zone 4, compact, densely-stemmed, clean, medium-green foliage that goes dormant in the winter;
4. Foliage and stems have white latex sap making the plants undesirable to deer and rabbits.

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
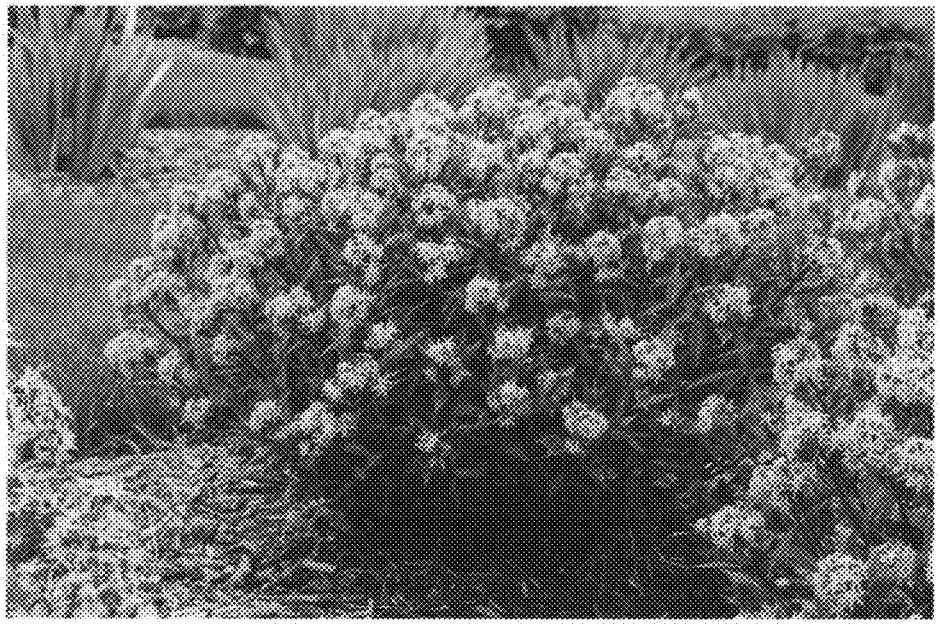
FIG. 1 shows an eight-year-old plant in peak flower during mid-summer in a full-sun trial garden in Zeeland, Mich.
Figure 2:
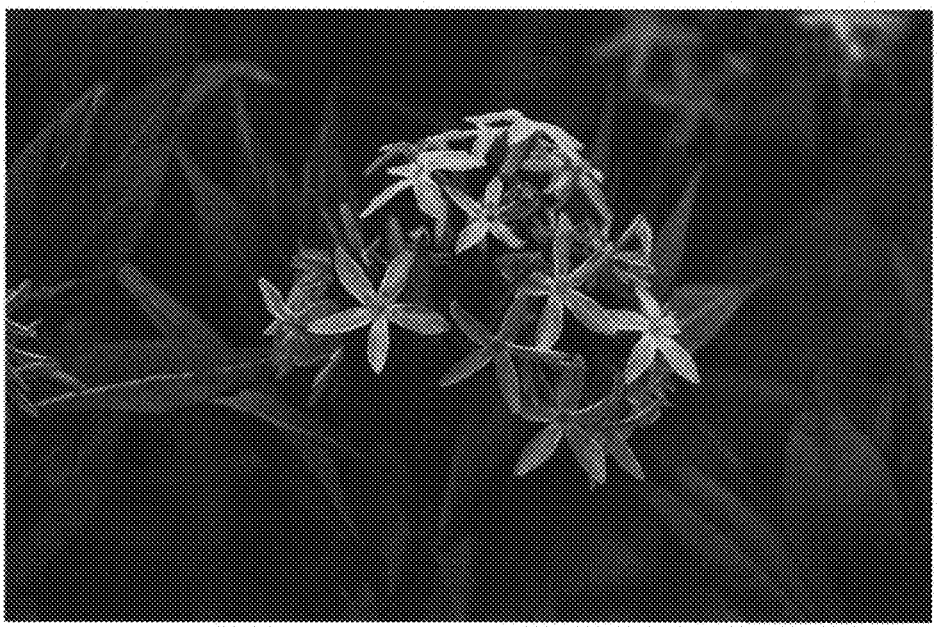
FIG. 2 shows a close-up of the flower and buds.

The following descriptions and color references are based on the 2015 edition of The Royal Horticultural Society Colour Chart except where common dictionary terms are used. The new plant, *Amsonia* 'Starstruck', has not been observed under all possible environments. The phenotype may vary slightly with different environmental conditions, such as temperature, light, fertility, moisture and maturity levels, but without any change in the genotype. The following observations and size descriptions are of an eight-year-old plant in a sunny research garden bed in Zeeland, Mich. with and supplemental water and fertilizer.

Botanical classification: *Amsonia* hybrid;

Parentage: female or seed parent is a proprietary unreleased selection of *A. rigida*; male or pollen parent is a proprietary unreleased selection of *A. tabernaemontana;*

Propagation: Division of the rhizome and shoot tip cuttings;

Growth rate: Moderate;

Crop time: About 15 to 20 weeks starting in early summer to grow a 2.5 cm plug to a flowering 3.8 liter container after vernalization;

Plant shape and habit: Winter-hardy herbaceous perennial with numerous stems with dark green foliage in a dense mound;

Plant size: Foliage height about 74 cm tall from soil line to the top of the flowers and about 107 cm wide about 25 cm above the soil;

Rooting habit: Primary roots thick, fleshy and seldom branched, to 30 cm long and 5.0 mm thick, color between RHS 165 B and RHS 165C; depending on soil type; secondary roots fibrous, to about 6 cm long and 1.0 mm diameter, color between RHS 158D and RHS 165D depending on soil type;

Leaves: Oblanceolate; sessile; alternate; entire; glabrous and glaucous both abaxial and adaxial; apex acute, base cuneate; about 24 leaves per stem; to about 5.5 cm long and 15.0 mm across near middle; attitude mostly outright;

Leaf color: Expanding adaxial nearest RHS 146A with tinting of nearest RHS N187A and abaxial nearest RHS 146B with tinting nearest RHS N187A; mature adaxial nearest a blend of RHS NN137B and RHS 137A, and abaxial nearest RHS 146A;

Veins: Pinnate; adaxial puberulent; abaxial glabrous;

Vein color: Mature and expanding adaxial midrib between RHS 151D and RHS145C secondary adaxial veins nearest RHS 146D; mature and expanding abaxial midrib RHS 146C and secondary veins nearest RHS 146D;

Stem: Cylindrical; glabrous; lustrous; to 46 cm tall and 6.0 mm diameter at base; with about 19 nodes per stems below flowering branches; average internode length about 2.4 cm;

Stem color: As emerging with leaves still tight nearest a blend between RHS 137A and RHS N187A; at flowering time lower portion nearest RHS 137B and upper portion a blend between RHS N187A and RHS NN137B;

Inflorescence: Branched panicle densely flowered in terminal portion; flowering about 8.0 cm across and 7.0 cm tall; about 30 to 50 flowers per panicle; inflorescences remain effective beginning early-May repeating for approximately four weeks in Zeeland, Mich.;

Flowers: Rotate, salverform; single; perfect; complete; actinomorphic; upward and outwardly facing; about 14.0 mm across in face and 8.0 mm tall, corolla tube about 7.0 mm long and 2.0 mm diameter; corona in center eye, about 4.0 mm across and 1.0 mm tall; individually lasting for about five to seven days; Flower fragrance: none detected;

Buds one to two days prior to opening: Ellipsoidal with rounded apex and base; about 9.0 mm long and about 2.0 mm in diameter at widest point with near middle;

Bud color one day from opening: Nearest RHS 91B;

Petals: Five; made up of fused corolla tube and perpendicular flattened limb; limb portion lanceolate, separate, not overlapping, with acute apex; limb portion about 6.0 mm long and 2.0 mm across; corolla tube puberulent in abaxial and distal 3.0 mm protruding above face in corona; also puberulent adaxial in the 2.0 mm below face, glabrous elsewhere;

Petal color: Adaxial face between RHS 91B and RHS 91C, with 1.0 mm center eye nearest RHS 96C; abaxial face between RHS 92C and RHS 92D; adaxial corolla tube distally nearest RHS 92C, center portion nearest RHS 138D and basal 2.0 mm nearest RHS 92C; abaxial corolla tube nearest RHS 96C distally, basal 4.0 mm between RHS 92B and RHS 92C, center portion between RHS 145A and RHS 146D; corona nearest RHS 97D; hairs nearest RHS NN155D;

Pedicel: Cylindrical; glabrous; lustrous; average about 3.0 mm long and 0.5 mm diameter; upright and outright;

Pedicel color: Nearest RHS 146A;

Peduncle: Cylindrical; glabrous; lustrous; typically one per division; just below flowering portion about 5.0 mm diameter at base, average 7.0 cm tall; extending above foliage; branches to about 3.5 cm long and 1.5 mm diameter;

Peduncle color: Between RHS 146D and RHS 144A proximally and strongly maculate distally to nearest RHS N187A;

Gynoecium: Single; about 6.0 mm long;

*Style*.—Single; cylindrical; glabrous; about 3.5 mm long, 0.3 mm diameter; color nearest RHS NN155D.

*Stigma*.—Globose; about 0.5 mm across; color nearest RHS 144A.

*Ovary*.—Superior; globose; about 1.3 mm long and 1.0 mm; color nearest RHS 138A.

Androecium: Five; adnate to inner corolla;

*Filaments*.—Five; adnate to inner corolla and extending about 6.0 mm to 7.0 mm above corolla base, and free in distal 1.0 mm; about 0.2 mm in diameter; color nearest RHS NN155D.

*Anthers*.—Oblong; basifixed, longitudinal; about 1.0 mm long and 0.5 mm wide; color closest to RHS N187A.

*Pollen*.—Abundant; color nearest RHS 158B.

Fruit: Slender; upright; non-fleshy; dried follicle; singled seeded in diameter; dehiscing along a longitudinal spiral; to about 10.0 cm long and 3.0 mm in diameter; color while maturing nearest RHS 138B and at dehiscence nearest RHS 164C;

Seed: Up to about 10 per follicle; cylindrical; apices and bases either truncate or angular; asperous; about 9.0 mm long, about 2.0 mm wide and about 1.0 mm thick; color nearest RHS 200D;

Disease and pest resistance and tolerance: 'Starstruck' shows typical Blue Star resistant to deer and rabbits but has not shown resistance to diseases and pests beyond that common for Blue Star plants. The plant grows best and shows best coloration with full-sun, plenty of moisture, adequate drainage, but is able to tolerate some drought when mature and direct sun without leaf burn when provided sufficient water.

Hardiness at least from USDA zone 4 through 9. The new plant is useful for landscaping en masse, as a single specimen or small groups, as a container plant or as a cut flower.

The invention claimed is:

1. A new and distinct ornamental Blue Star, *Amsonia* plant named 'Startstruck' as herein described and illustrated.

* * * * *